United States Patent [19]

Worthington

[11] 4,443,455
[45] Apr. 17, 1984

[54] FUNGIDICAL THIAZOLIDINONES

[75] Inventor: Paul A. Worthington, Maidenhead, England

[73] Assignee: Imperial Chemical Industries PLC, London, England

[21] Appl. No.: 224,669

[22] Filed: Jan. 13, 1981

Related U.S. Application Data

[62] Division of Ser. No. 11,051, Feb. 9, 1979.

[30] Foreign Application Priority Data

Feb. 17, 1978 [GB] United Kingdom ................. 6486/78

[51] Int. Cl.$^3$ ..................... A01N 43/78; A01N 43/40; C07D 401/04
[52] U.S. Cl. ..................................... 424/263; 546/280
[58] Field of Search ........................ 424/263; 546/280; 71/90

[56] References Cited

U.S. PATENT DOCUMENTS

| | | | |
|---|---|---|---|
| 2,839,404 | 6/1958 | Knott | 546/280 |
| 4,017,628 | 4/1977 | Nitidandhaprabhas | 424/263 |
| 4,053,471 | 10/1977 | Krapcho | 544/133 |
| 4,062,859 | 12/1977 | Weiler et al. | 260/302 A |
| 4,067,878 | 1/1978 | Miller et al. | 260/302 A |
| 4,080,457 | 3/1978 | Harrison et al. | 424/263 |
| 4,150,026 | 4/1979 | Miller et al. | 260/299 |

FOREIGN PATENT DOCUMENTS

| | | |
|---|---|---|
| 845519 | 9/1975 | Belgium . |
| 847760 | 10/1975 | Belgium . |
| 4129 | 9/1979 | European Pat. Off. ............ 546/280 |
| 48-17276 | 5/1973 | Japan . |
| 2031892 | 4/1980 | United Kingdom ................ 546/280 |

OTHER PUBLICATIONS

Fenech, Chemical Abstracts, vol. 54:24723e.
Fenech et al., Chemical Abstracts, vol. 55:15465-6, (1961).
Fenech, Chemical Abstracts, vol. 65:4439-40, (1966).
Fenech et al., Chemical Abstracts, vol. 71:9716m, (1969).
Vigorita et al., Chemical Abstracts, vol. 76:152784r, (1972).
Deikalo et al., Chemical Abstracts, vol. 78:43343s, (1978).
Seiji, Miyano et al., Chemical Abstracts, vol. 79:78784j, (1978).
Krumkalns, South Africa Pat. Application No. 795488, (10/1979).

Primary Examiner—John M. Ford
Attorney, Agent, or Firm—Cushman, Darby & Cushman

[57] ABSTRACT

A process for combating plant fungi with a thiazolidinone of the formula:

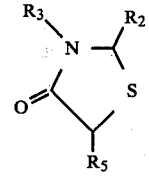

or a fungicidal salt or complex thereof, wherein $R_3$ is 3-pyridyl and $R_2$ is phenyl or a substituted phenyl and $R_5$ is hydrogen or alkyl, and an inert carrier therefor, provided that when $R_5$ is hydrogen, $R_2$ is not phenyl or 2-chlorophenyl.

1 Claim, No Drawings

FUNGICIDAL THIAZOLIDINONES

This is a division of application Ser. No. 11,051 filed Feb. 9, 1979.

TREATING PLANTS

This invention relates to thiazolidinone compounds, having pesticidal and plant growth regulating properties; and to methods for making them.

The invention provides thiazolidinone compounds having the general formula (I):

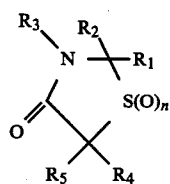

and salts and complexes thereof, wherein $R_1$, $R_4$ and $R_5$ are hydrogen, or hydrocarbyl; one of $R_2$ and $R_3$ is optionally substituted 3-pyridyl and the other is optionally substituted 3-pyridyl or hydrocarbyl; and n is 0, 1 or 2; provided that when $R_3$ is 3-pyridyl and $R_1$, $R_4$ and $R_5$ are hydrogen, $R_2$ is not phenyl or 2-chlorophenyl.

In a preferred aspect the invention provides thiazolidinone compounds having the general formula:

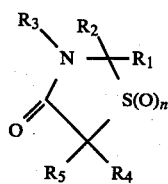

and salts and complexes thereof, wherein $R_1$, $R_4$ and $R_5$ are hydrogen or hydrocarbyl; $R_2$ is optionally substituted 3-pyridyl; $R_3$ is hydrocarbyl; and n is 0, 1 or 2.

Suitable salts are salts with inorganic or organic acids, e.g. hydrochloric, nitric, sulphuric, toluenesulphonic, acetic or oxalic acid.

The metal complex is suitably one including copper, zinc, manganese or iron.

When $R_1$, $R_4$ and $R_5$, and either $R_2$ or $R_3$ are hydrocarbyl groups they are preferably simple hydrocarbyl radicals in view of the ready availability of these. It is to be understood however that the whole range of hydrocarbyl groups, unsubstituted or substituted, is considered to fall within the scope of this invention since the particular nature of the hydrocarbyl group, if one is present, is not believed to be critically important. Thus the hydrocarbyl groups may be saturated or unsaturated, straight or branched chain, single-ring or multi-ring; thus $R_1$, $R_4$ and $R_5$ may be, for example, alkyl, alkenyl, alkynyl, cycloalkyl, aryl, aralkyl, or alkaryl groups, for example methyl, ethyl, propyl, butyl, cyclohexyl, allyl or propynyl groups, and one or more of their hydrogen atoms may be substituted by simple substituents, such as, for example, halogen atoms, for example chlorine, bromine and fluorine, or pseudo halogen groups such as, for example cyano, or groups such as amino, hydroxy, nitro, phenyl and mercapto groups (which may themselves bear substituents). When $R_1$, $R_4$ and $R_5$ are alkyl groups, preferred alkyl groups are straight or branched chain groups having 1 to 4 carbon atoms and especially 1 or 2 carbon atoms; examples are methyl, ethyl, propyl and n-, iso- or t-butyl.

When $R_1$, $R_2$, $R_3$, $R_4$ or $R_5$ is an aryl group it may be, for example, phenyl or naphthyl, optionally substituted, with, for example, one or more halogen atoms or alkyl, trifluoroalkyl, alkoxy, hydroxy, nitro, amino, cyano or mercapto groups. These substituent groups may themselves bear substituents. When $R_2$ or $R_3$ is 3-pyridyl the pyridine ring may be substituted, for example with one or more of the foregoing substituent groups recited above.

In a more preferred aspect the invention provides thiazolidinone compounds having the general formula (II):

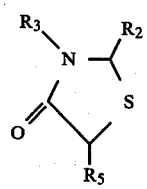

and salts and complexes thereof, wherein $R_2$ is 3-pyridyl and $R_3$ is phenyl or phenyl substituted with one or more halogen atoms or alkyl or haloalkyl groups having 1 to 4 carbon atoms and $R_5$ is hydrogen or alkyl having 1 to 4 carbon atoms.

In an even more preferred aspect the invention provides thiazolidinone compounds of the general formula:

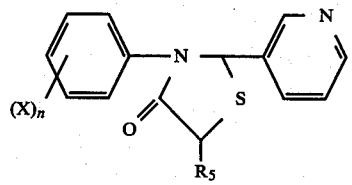

and salts and complexes thereof, wherein X is halogen, especially chlorine, and n is 0, 1 or 2; and $R_5$ is hydrogen or methyl.

In a particularly preferred aspect the invention provides the compound having the formula (III):

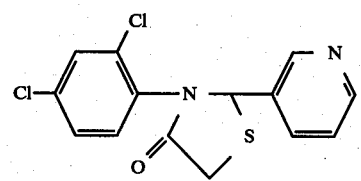

and salts and complexes thereof.

The invention is illustrated by the specific compounds set out in Table I below, and corresponding to the general formula (IV):

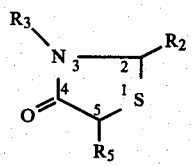

in which the numbering of the ring atoms is shown.

TABLE I

| COMPOUND NO | R₂ | R₃ | R₅ | MELTING POINT (DEGREES CENTIGRADE) |
|---|---|---|---|---|
| 1 | 3-pyridyl | 4-chlorophenyl | H | 171–171.5° |
| 2 | 4-chlorophenyl | 3-pyridyl | H | 131–132° |
| 3 | 3-pyridyl | phenyl | H | 188–189° |
| 4 | 3-pyridyl | 4-chlorophenyl | H | 153–154° |
| 5 | 4-chlorophenyl | 3-pyridyl | CH₃ | 146–147° |
| 6 | 3-pyridyl | 3-chlorophenyl | H | 158–160° |
| 7 | 3-pyridyl | 2-chloro-4-methylphenyl | H | 180–181° |
| 8 | 3-pyridyl | 2-methylphenyl | H | 168–170° |
| 9 | 3-pyridyl | 2-fluorophenyl | H | 140–141° |
| 10 | 3-pyridyl | 2,4-dimethylphenyl | H | 67–70° |
| 11 | 3-pyridyl | 2-bromophenyl | CH₃ | 148–149° |
| 12 | 3-pyridyl | 2-methyl-5-chlorophenyl | H | 128–130° |

TABLE I-continued

| COMPOUND NO | $R_2$ | $R_3$ | $R_5$ | MELTING POINT (DEGREES CENTIGRADE) |
|---|---|---|---|---|
| 13 | 3-pyridyl | 3-(CF₃)phenyl | H | 83–84° |
| 14 | 3-pyridyl | 3,5-dichlorophenyl | H | 155–156° |
| 15 | 3,4-dichlorophenyl | 3-pyridyl | H | 78–79° |
| 16 | 3-pyridyl | 3,4-dichlorophenyl | =CH—C₆H₅ | 137–138° |
| 17 | 3-pyridyl | 2,3-dichlorophenyl | H | 164–165° |
| 18 | 3-pyridyl | 2-chlorophenyl | H | 129–130° |

The invention is further illustrated by the specific compounds set out in Table II below, and corresponding to the general formula:

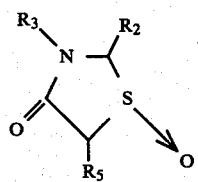

TABLE II

| COMPOUND NO | $R_2$ | $R_3$ | $R_5$ | MELTING POINT (DEGREES CENTIGRADE) |
|---|---|---|---|---|
| 19 | 3-pyridyl | 3-methylphenyl | H | 214–215° |
| 20 | 3-pyridyl | 4-methylphenyl | H | 214–215° |
| 21 | 3-pyridyl | 4-fluorophenyl | H | 213–214° |
| 22 | 3-pyridyl | 3-methyl-4-chlorophenyl | H | 198–199° |
| 23 | 3-pyridyl | 3-(CF₃)phenyl | H | 97–98° |

TABLE II-continued

| COMPOUND NO | R2 | R3 | R5 | MELTING POINT (DEGREES CENTIGRADE) |
|---|---|---|---|---|
| 24 |  (pyridyl) |  (dichlorophenyl) | H | 185–186° |
| 25 |  (pyridyl) |  (phenyl) | H | 204–205 |
| 26 |  (chloropyridyl) |  (chlorophenyl) | H | 173–174° |

The invention is further illustrated by the specific compounds set out in Table III below, and corresponding to the general formula:

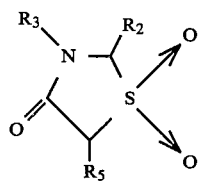

TABLE III

| COMPOUND NO | R2 | R3 | R5 | MELTING POINT (DEGREES CENTIGRADE) |
|---|---|---|---|---|
| 27 | (pyridyl) | (chlorophenyl) | H | 139–140° |
| 28 | (pyridyl) | (phenyl) | H | 207–208° |
| 29 | (pyridyl) | (chlorophenyl with Cl) | H | 188–189° |

The compounds of the invention may be made by reacting the appropriate aldehyde (V) and amine (VI) with an α-mercapto fatty acid (VII) in a high boiling solvent such as benzene, toluene or chlorobenzene (toluene is preferred); and wherein

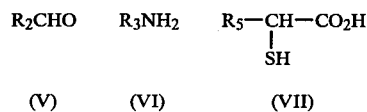

(V)  (VI)  (VII)

R2, R3 and R5 are as defined above. The product can be isolated by removing the solvent and recrystallising the residue from a convenient solvent.

The compounds of general formula (II) may also be made by reacting the imine (VIII) (preformed from the aldehyde (V) and amine (VI) by methods set out in the literature) with the α-mercapto fatty acid (VII) in a high boiling solvent (preferably toluene).

(VIII)

α-mercapto thiofatty acids can be used in addition to α-mercapto fatty acids (VII) to form the compounds of the invention. These are made by methods set out in the literature.

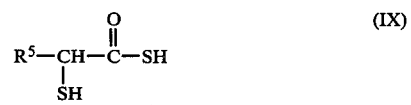

(IX)

The thiazolidinone sulphoxides (X) may be made by oxidising the corresponding thiazolidinone (II) with a conventional oxidising agent such as hydrogen peroxide, peracids (e.g. metachloroperbenzoic acid or peracetic acid), or potassium permanganate. In a specific example the thiazolidinone was dissolved in a chlorinated hydrocarbon solvent (chloroform or dichloromethane) and oxidised at 0° C. with metachloroperbenzoic acid. The product was isolated by removing the solvent and recrystallising the residue from a convenient solvent.

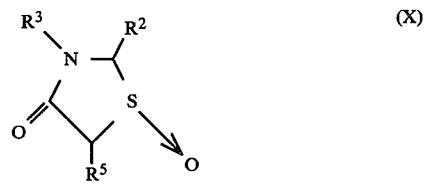

(X)

The thiazolidinone sulphones (XI) may be made by oxidising the corresponding thiazolidinone (II) or the thiazolidinone sulphoxide (X) with a conventional oxidising agent such as hydrogen peroxide, peracids (e.g. metachloroperbenzoic acid or peracetic acid), or potassium permanganate at elevated temperatures. In a specific example the thiazolidinone was dissolved in acetic acid and oxidised with a solution of potassium permanganate in water at 20°. The product was precipitated out of solution by addition of sodium metabisulphite and recrystallised from a convenient solvent.

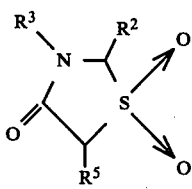

The invention further provides methods for making the compounds according to the invention by the foregoing processes.

The thiazolidinone compounds of the invention display, variously, activity against the following diseases:

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants, *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines, *Cercospora arachidicola* on peanuts and other Cercospora species on for example sugar beet, bananas and soya beans, *Botrytis cinerea* (grey mould) on tomatoes, strawberries, vines and other hosts, *Phytophthora infestans* (blight) on tomatoes and potatoes *Venturia inaequalis* (scab) on apples They can be used as industrial (as opposed to agricultural) fungicides, e.g. as paint film fungicides. The compounds also have plant growth regulating properties.

The compounds also have algicidal, anti-bacterial and anti-viral activities; and also herbicidal activity.

The compounds may be used as such, for example for the fungicidal or plant growth regulating or herbicidal or other purposes but are more conveniently formulated into compositions for such usage.

The invention compounds and salts and complexes thereof, can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butynaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending on the intended purpose, but an aqueous preparation containing 0.0005% or 0.01% to 10% by weight of active ingredient(s) may be used.

The compositions can comprise also other compound(s) having biological activity [e.g. other growth stimulating substances such as the gibberellins (e.g. $GA_3$, $GA_4$ or $GA_7$), the auxins (e.g. indoleacetic or indolebutyric acid) and the cytokinins (e.g. kinetin, diphenylurea, benzimidazole and benzyladenine) and other compounds having complementary fungicidal or insecticidal activity], as well as stabilising agent(s), for example epoxides (e.g. epichlorohydrin).

The following Examples illustrate the invention; the temperatures are given in degrees Centigrade (°).

EXAMPLE 1

This Example illustrates the preparation of 2-(3-pyridyl)-3-(2,4-dichlorophenyl)-thiazolid-4-one. (Compound No. 1 of Table I).

3-pyridine aldehyde (0.1 mol), 2,4-dichloroaniline (0.1 mol) and mercaptoacetic acid (0.1 mol) were refluxed in toluene (150 ml) for 6 hours and the water removed using a Dean and Stark apparatus. Removal of the toluene in vacuo gave a yellow oil which solidified on trituration with ethanol. Recrystallisation from ethanol gave the title compound as a fine white crystalline solid m.p. 171°–175° C.

EXAMPLE 2

This Example illustrates the preparation of 2-(4-chlorophenyl)-3-(3-pyridyl)-thiazolid-4-one. (Compound No. 3 of Table I).

3-aminopyridine (0.1 mol), 4-chlorobenzaldehyde (0.1 mol), and mercaptoacetic acid (0.1 mol) were refluxed in toluene (150 ml) for 4 hours and the water was removed using a Dean and Stark apparatus. Removal of the toluene in vacuo gave a yellow solid which was washed with 60–80 petroleum ether ($4 \times 100$ ml). Recrystallisation of the solid from ethanol gave the title compound as a colourless crystalline solid m.p. 131°–132°.

EXAMPLE 3

This Example illustrates the preparation of 2-(4-chlorophenyl)-3-(3-pyridyl)-5-methyl-thiazolid-4-one. (Compound No. 6 of Table I).

3-Aminopyridine (0.1 mol) and 4-chlorobenzaldehyde (0.1 mol) were dissolved in toluene (150 ml). Thiolactic acid (0.1 mol) was added and the solution refluxed in a Dean and Stark apparatus for 4 hours. Removal of the toluene in vacuo gave a dark brown oil which solidified on trituration with ethanol. Recrystallisation from ethanol gave the title compound as a colourless crystalline solid m.p. 146°–147°.

EXAMPLE 4

This Example illustrates the preparation of the compound 2-(3-pyridyl)-3-(2,4-dichlorophenyl)-thiazolidin-1-oxide-4-one (Compound No. 27 of Table II).

M-chloroperbenzoic acid (0.1 mol) was dissolved in dichloromethane (100 ml). 2-(3-Pyridyl)-3-(2,4-dichlorophenyl-thiazolidin-4-one (0.1 mol) was added portionwise at such a rate that the temperature did not rise above 10° C. After stirring at room temperature for 2 hours the solution was filtered and the filtrate washed with saturated sodium bicarbonate ($2 \times 500$ ml), water ($2 \times 500$ ml), and dried over anhydrous sodium sulphate. Removal of the solvent gave a white solid which on recrystallisation from chloroform/ethanol gave the title compound as colourless crystals m.p. 173°–174°.

EXAMPLE 5

This Example illustrates the preparation of 2-(3-pyridyl)-3-(2,4-dichlorophenyl)-thiazolidin-1,1-dioxide-4-one (Compound No. 30 of Table III).

2-(3-Pyridyl)-3-(2,4-dichlorophenyl)-thiazolidin-4-one (0.05 mol) was dissolved in glacial acetic acid (150 ml). A solution of powdered potassium permanganate (0.15 mol) in water (500 ml) was added dropwise at 15°–20° over a period of 30 minutes and the solution stirred at 20° for a further 2 hours until the permanganate colour was discharged. This solution was added dropwise to a solution of sodium metabisulphite (100 g) in water (1000 ml), a white crystalline solid was produced. The solid was filtered off and washed with water ($3 \times 500$ ml). Recrystallisation from chloroform/ethanol gave the title compound as a colourless crystalline solid m.p. 188°–189°.

EXAMPLE 6

This Example lists a number of pesticidal compositions containing the invention compounds.

| (1) Dispersible Powder | |
|---|---|
| Compound 1 (of Table 1) | 50% wt/wt |
| Aerosol OT | 2% |
| Polyfon H | 5% |
| China Clay | 43% |
| (2) Emulsifiable Concentrate | |
| Compound 1 | 100 g/liter |
| Amine dodecylbenzene sulphonate | 400 g/liter |
| 2-n-Butoxyethanol | to 1 liter |
| (3) Aqueous Suspension | |
| Compound 1 | 250 g/liter |
| Polyfon H | 25 g/liter |
| Bentonite | 15 |
| Polysaccharide | 0.75 |
| Water | to 1 liter |
| (4) Dust | |
| Compound 1 | 5% wt/wt |
| China Clay | 95% |
| (5) Granules | |
| Compound 1 | 5% wt/wt |
| Starch | 5% |
| China Clay | 90% |
| (6) Solvent Solution | |
| Compound 1 | 200 g/liter |
| Dimethylformamide | to 1 liter |

The other compounds of Tables I, II and III were similarly formulated.

EXAMPLE 7

The thiazolidinone compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. Exceptions were the tests on *Phytophthora infestans*, *Venturia inaequalis* and *Podosphaera leucotricha* where the suspensions were sprayed on to the foliage only. For the latter diseases the concentrations of the compound were 25 and 10 ppm respectively, whilst for Uncinula necator the rate was 5 ppm. (Sprays were applied to maximum retention, and root drenches to a final concentration equivalent to approximately 40 ppm a.i./dry soil). Tween 20, to give a final concentration of 0.05%, was added when the sprays were applied to the cereals.

For most of the tests, the test compound was applied to the soil (roots) and to the foliage (by spraying) one or two days before the plant was inoculated with the diseases. Exceptions were the tests on *Erysiphe graminis*, *Uncinula necator* and *Podosphaera leucotricha* in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:

4=No disease
3=0–5%
2=6–25%
1=26–60%
0=>60%

The results are shown in Table IV.

TABLE IV

| COMPOUND NO | PUCCINIA RECONDITA (WHEAT) | ERYSIPHE GRAMINIS (BARLEY) | PIRICULARIA ORYZAE (RICE) | CERCOSPORA ARACHIDICOLA (PEANUT) |
|---|---|---|---|---|
| 1 | 3 | 4 | 0 | 4 |
| 2 | 0 | 4 | 0 | 2 |
| 3 | 0 | 4 | 0 | 0 |
| 4 | 0 | 4 | 1 | 0 |
| 5 | 1 | 4 | 3 | — |
| 6 | 0 | 4 | 0 | 0 |
| 7 | 0 | 4 | 0 | 0 |
| 8 | 0 | 4 | 0 | 0 |
| 9 | 0 | 4 | 2 | 1 |
| 10 | 0 | 3 | 0 | 0 |
| 11 | 0 | 3 | 0 | 0 |
| 12 | 0 | 4 | 1 | 0 |
| 13 | 0 | 3 | 0 | 0 |
| 14 | 0 | 3 | 0 | — |
| 15 | 0 | 4 | 0 | 3 |
| 16 | 3 | 4 | 2 | 1 |
| 17 | 0 | 3 | 2 | 2 |
| 18 | 0 | 4 | 0 | 2 |
| 19 | 0 | 0 | 1 | 0 |
| 20 | 0 | 4 | 2 | 2 |
| 21 | 0 | 4 | 2 | 0 |
| 22 | 3 | 4 | — | 4 |
| 23 | 0 | 0 | 1 | 1 |
| 24 | 0 | 4 | 1 | — |
| 25 | 0 | 3 | 0 | — |
| 26 | 3 | 4 | 1 | 4 |
| 27 | 0 | 4 | — | — |
| 28 | 1 | 4 | 0 | — |
| 29 | 0 | 4 | 3 | 4 |

| COMPOUND NO | PODOSPHAERA LEUCOTRICHA (APPLE) | PHYTOPHTHORA INFESTANS (TOMATO) | BOTRYTIS CINEREA (TOMATO) | VENTURIA INAEQUALIS (APPLE) | UNCINULA NECATOR (VINE) |
|---|---|---|---|---|---|
| 1 | 4 | 0 | 4 | 4 | 4 |
| 2 | — | 3 | — | — | — |
| 3 | 0 | 0 | — | 0 | 0 |
| 4 | 1 | 0 | 3* | 1-2 | 3 |
| 5 | 2 | 0 | 2 | 1 | 1 |
| 6 | 0 | 0 | 0 | 0 | 0 |
| 7 | 0 | 0 | 2 | 0 | 1 |
| 8 | — | 0 | 0 | 1 | — |
| 9 | — | 0 | 0 | 2 | — |
| 10 | — | 2 | 0 | 0 | — |
| 11 | — | 4 | 1 | 3 | — |
| 12 | 4 | 0 | 3 | 3 | — |
| 13 | 3 | 0 | 0 | 0 | 2 |
| 14 | 0 | 0 | 1 | 0 | 1 |
| 15 | — | 0 | 4 | 3 | — |
| 16 | — | 0 | 0 | 0 | — |

TABLE IV-continued

| | | | | | |
|---|---|---|---|---|---|
| 17 | — | 1 | 0 | 0 | — |
| 18 | — | 0 | 1 | 4 | — |
| 19 | — | 0 | 0 | 0 | — |
| 20 | — | 0 | 0 | 2 | 0 |
| 21 | — | 0 | 0 | 3 | — |
| 22 | — | 0 | 0 | 0 | — |
| 23 | 1 | 0 | 1 | 1 | 0 |
| 24 | 1 | 0 | 0 | 0 | 2 |
| 25 | — | 0 | 0 | 0 | — |
| 26 | 0 | 0 | 1 | 2 | 4 |
| 27 | — | 1 | 0 | 0 | — |
| 28 | — | 0 | 0 | 0 | — |
| 29 | 4 | 1 | 1 | 3 | 4 |

"—" means not tested.
"*" signifies rate of application of 50 ppm.

I claim:

1. A process for combating plant fungi which comprises treating the fungi with a fungicidally effective amount of a thiazolidinone compound of the formula:

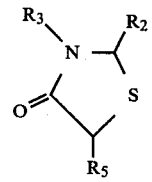

or a fungicidal salt or complex thereof, wherein $R_3$ is 3-pyridyl and $R_2$ is phenyl or phenyl substituted with one or more halogen atoms, or alkyl or haloalkyl groups having from 1 to 4 carbon atoms and $R_5$ is hydrogen or alkyl having 1 to 4 carbon atoms and an inert carrier therefor, provided that when $R_5$ is hydrogen, $R_2$ is not phenyl or 2-chlorophenyl.

* * * * *

UNITED STATES PATENT AND TRADEMARK OFFICE
CERTIFICATE OF CORRECTION

PATENT NO. : 4,443,455
DATED : April 17, 1984
INVENTOR(S) : Paul Anthony WORTHINGTON It is certified that error appears in the above-identified patent and that said Letters Patent are hereby corrected as shown below:

In the heading of the patent:

--[54] Change "FUNGIDICAL" to --FUNGICIDAL--

[30] Foreign Application Priority Data

Add:

--Nov. 14, 1978 [GB]  United Kingdom.....44362/78--

Signed and Sealed this

Twenty-fourth Day of September 1985

[SEAL]

Attest:

DONALD J. QUIGG

*Attesting Officer*

*Commissioner of Patents and Trademarks—Designate*